(12) United States Patent
Sheu et al.

(10) Patent No.: US 7,838,048 B2
(45) Date of Patent: Nov. 23, 2010

(54) MEDICAL HERB COMPOSITION FOR INHIBITING SHEDDING OF A MAMMAL'S HAIR AND METHOD FOR PREPARING THE SAME

(75) Inventors: Shuenn-Jyi Sheu, Taipei (TW); Ching-Che Lin, Taipei (TW); Hsiao-Yin Yeh, Taipei (TW); Chen-Ying Chiang, Taipei (TW)

(73) Assignee: Brion Research Institute of Taiwan, Taipei (TW)

( * ) Notice: Subject to any disclaimer, the term of this patent is extended or adjusted under 35 U.S.C. 154(b) by 0 days.

(21) Appl. No.: 12/318,677

(22) Filed: Jan. 6, 2009

(65) Prior Publication Data

US 2010/0173023 A1 Jul. 8, 2010

(51) Int. Cl.
*A61K 36/232* (2006.01)
*A61K 36/481* (2006.01)
*A61K 36/638* (2006.01)
*A61K 36/804* (2006.01)

(52) U.S. Cl. .................................. 424/725; 424/773

(58) Field of Classification Search ................. None
See application file for complete search history.

(56) References Cited

U.S. PATENT DOCUMENTS

2007/0292451 A1* 12/2007 Sheu et al. ............. 424/195.15

FOREIGN PATENT DOCUMENTS

| CN | 1078903 A | * | 12/1993 |
| CN | 1089850 A | * | 7/1994 |
| CN | 1883640 A | * | 12/2006 |
| KR | 2001-0100602 | * | 5/2002 |

OTHER PUBLICATIONS http://www.fzrm.com/plantextracts/Yerbadetajo_Herb_extract.htm—accessed Sep. 2009.*

* cited by examiner

*Primary Examiner*—Susan C Hoffman
(74) *Attorney, Agent, or Firm*—Bacon & Thomas PLLC

(57) ABSTRACT

The present invention relates to a medical herb composition for reducing shedding of mammal hair and a method for preparing the same. The medical herb composition comprises: a first herb material selected from the group consisting of Ginseng Radix, Astragali Radix, Batatatis Rhizoma, Zizyphi Fructus, *Tremella, Codonopsis Pilosula*, or the combination thereof; a second herb material selected from the group consisting of Angelicae Radix, Rehmanniae Preparata Radix, Longanae Arillus, Lycii Fructus, *Paeonia lactiflora*, or the combination thereof; and a third herb material selected from the group consisting of Rehmanniae Radix, *Ligustrum Lucidum, Eclipta prostrata, Dendrobium hancockii, Polygonum multiflorun* (i.e. *Dioscorea bulbifera* or *Cynanchum wilfordi*), or the combination thereof. The medical herb composition of the present invention can reduce shedding of mammal hair, promote the growth of hair, and also can efficiently improve vitality, skin condition, and complexion.

14 Claims, 7 Drawing Sheets

| Subject | Gender | Age | Weight | Prescription | Exempting alopecia | Growing hair | Vitality improvement | Good complexion |
|---|---|---|---|---|---|---|---|---|
| Mr. Huang | M | 29 | 65 | *Eclipta prostrate* | 1 | 0 | 1 | 0 |
| Mr. Su | M | 45 | 84 | *Eclipta prostrate* | 0 | 2 | 2 | 0 |
| Mr. Liao | M | 50 | 66 | *Eclipta prostrate* | 0 | 1 | 0 | 0 |
| Mr. Chao | M | 38 | 60 | *Eclipta prostrate* | 2 | 0 | 1 | 2 |
| Mr. Shih | M | 32 | 74 | *Eclipta prostrate* | 1 | 0 | 0 | 1 |
| Mr. Lu | M | 41 | 82 | *Eclipta prostrate* | 2 | 0 | 0 | 1 |
| Average effect | | | | | 1.0 | 0.5 | 0.7 | 0.7 |

FIG 1

| Subject | Gender | Age | Weight | Prescription | Exempting alopecia | Growing hair | Vitality improvement | Good complexion |
|---|---|---|---|---|---|---|---|---|
| Mr. Huang | M | 41 | 69 | A1 | 5 | 5 | 5 | 5 |
| Ms. Kao | F | 45 | 60 | A1 | 5 | 4 | 5 | 5 |
| Mr. Chou | M | 43 | 72 | A1 | 5 | 4 | 2 | 2 |
| Ms. Hsu | F | 55 | 42 | A1 | 4 | 2 | 4 | 4 |
| Mr. Cheng | M | 34 | 91 | A1 | 4 | 2 | 2 | 2 |
| Mr. Chen | M | 37 | 68 | A1 | 5 | 2 | 3 | 3 |
| Mr. Hsieh | M | 38 | 59 | A1 | 4 | 1 | 3 | 3 |
| Mr. Lin | M | 37 | 76 | A1 | 3 | 1 | 3 | 1 |
| Ms. You | F | 25 | 59 | A1 | 2 | 1 | 3 | 1 |
| Average effect | | | | | 4.1 | 2.4 | 3.3 | 2.9 |

FIG 2

| Subject | Gender | Age | Weight | Prescription | Exempting alopecia | Growing hair | Vitality improvement | Good complexion |
|---|---|---|---|---|---|---|---|---|
| Mr. Chiu | M | 31 | 55 | A2 | 5 | 5 | 3 | 3 |
| Mr. Liang | M | 38 | 95 | A2 | 5 | 5 | 4 | 3 |
| Mr. Huang | M | 33 | 80 | A2 | 5 | 5 | 5 | 5 |
| Mr. Lu | M | 29 | 80 | A2 | 5 | 3 | 4 | 2 |
| Mr. Chen | M | 40 | 64 | A2 | 4 | 3 | 5 | 4 |
| Ms. Chao | F | 40 | 45 | A2 | 5 | 2 | 5 | 2 |
| Mr. Yang | M | 32 | 67 | A2 | 4 | 1 | 2 | 1 |
| Mr. Liu | M | 28 | 54 | A2 | 3 | 1 | 3 | 0 |
| Mr. Wen | M | 47 | 55 | A2 | 3 | 1 | 3 | 0 |
| Average effect | | | | | 4.3 | 2.9 | 3.8 | 2.2 |

FIG 3

| Subject | Gender | Age | Weight | Prescription | Exempting alopecia | Growing hair | Vitality improvement | Good complexion |
|---------|--------|-----|--------|--------------|--------------------|--------------|----------------------|-----------------|
| Mr. Lin | M | 29 | 70 | A3 | 5 | 5 | 5 | 4 |
| Mr. Ho | M | 53 | 71 | A3 | 5 | 5 | 5 | 5 |
| Mr. Hsu | M | 38 | 68 | A3 | 5 | 5 | 5 | 5 |
| Mr. Wen | M | 40 | 55 | A3 | 5 | 3 | 5 | 5 |
| Ms. Lu | F | 30 | 43 | A3 | 4 | 3 | 5 | 4 |
| Mr. Tsai | M | 35 | 68 | A3 | 5 | 2 | 4 | 3 |
| Mr. Chou | M | 41 | 67 | A3 | 4 | 1 | 3 | 3 |
| Mr. Hung | M | 39 | 50 | A3 | 3 | 1 | 3 | 1 |
| Mr. Wang | M | 37 | 61 | A3 | 3 | 1 | 2 | 1 |
| Average effect | | | | | 4.3 | 2.9 | 4.1 | 3.4 |

FIG 4

| Subject | Gender | Age | Weight | Prescription | Exempting alopecia | Growing hair | Vitality improvement | Good complexion |
|---|---|---|---|---|---|---|---|---|
| Mr. Yen | M | 60 | 58 | A4 | 5 | 5 | 5 | 5 |
| Mr. Chang | M | 58 | 60 | A4 | 5 | 5 | 5 | 5 |
| Mr. Chou | M | 40 | 75 | A4 | 5 | 5 | 5 | 5 |
| Mr. Lin | M | 42 | 84 | A4 | 5 | 5 | 5 | 5 |
| Ms. Yang | F | 38 | 49 | A4 | 5 | 4 | 4 | 2 |
| Mr. Liao | M | 43 | 68 | A4 | 5 | 4 | 4 | 2 |
| Mr. Hsu | M | 23 | 62 | A4 | 3 | 1 | 3 | 2 |
| Mr. Lee | M | 31 | 66 | A4 | 3 | 1 | 3 | 1 |
| Mr. Hsu | M | 25 | 65 | A4 | 4 | 1 | 3 | 1 |
| Mr. Chi | M | 38 | 65 | A4 | 4 | 1 | 3 | 1 |
| Average effect | | | | | 4.4 | 3.2 | 4.0 | 2.9 |

FIG 5

| Subject | Gender | Age | Weight | Prescription | Exempting alopecia | Growing hair | Vitality improvement | Good complexion |
|---------|--------|-----|--------|--------------|--------------------|--------------|----------------------|-----------------|
| Ms. Yeh | F | 26 | 47 | A5 | 5 | 5 | 5 | 5 |
| Mr. Chang | M | 34 | 62 | A5 | 5 | 4 | 3 | 2 |
| Mr. Chao | M | 35 | 83 | A5 | 5 | 3 | 2 | 2 |
| Mr. Chan | M | 39 | 60 | A5 | 4 | 3 | 3 | 2 |
| Mr. Chen | M | 37 | 64 | A5 | 5 | 2 | 5 | 2 |
| Mr. Chang | M | 30 | 83 | A5 | 2 | 1 | 2 | 2 |
| Average effect | | | | | 4.3 | 3.0 | 3.3 | 2.5 |

FIG 6

| Subject | Gender | Age | Weight | Prescription | Exempting alopecia | Growing hair | Vitality improvement | Good complexion |
|---|---|---|---|---|---|---|---|---|
| Mr. Chiu | M | 36 | 72 | A6 | 5 | 5 | 4 | 3 |
| Mr. Hsu | M | 40 | 65 | A6 | 5 | 4 | 3 | 1 |
| Mr. Chang | M | 48 | 60 | A6 | 3 | 2 | 5 | 5 |
| Ms. Tuan | F | 39 | 46 | A6 | 5 | 2 | 4 | 5 |
| Mr. Liu | M | 31 | 87 | A6 | 3 | 1 | 4 | 2 |
| Mr. Pan | M | 30 | 86 | A6 | 2 | 1 | 3 | 1 |
| Average effect | | | | | 3.8 | 2.5 | 3.8 | 2.8 |

FIG 7

MEDICAL HERB COMPOSITION FOR INHIBITING SHEDDING OF A MAMMAL'S HAIR AND METHOD FOR PREPARING THE SAME

BACKGROUND OF THE INVENTION

1. Field of the Invention

The present invention relates to a medical herb composition and a method for preparing the same and, more particularly, to a medical herb composition for reducing shedding, promoting hair growth and vitality in a mammal, and a method for preparing the same.

2. Description of Related Art

According to traditional Chinese herb material science theory, it is considered that: the human kidney is the root of innate endowment, and the essence is hair. Therefore the growth and shedding process of human hair reflects the exuberance and debilitation of the essential qi in the kidney. The hair of people whose kidney qi is flourishing is luxuriant and shiny, and the hair of people whose kidney qi is insufficient is easy to fall out, become shrivelled and turn to white. The growth, falling out, glossiness and haggardness of hair are not only respectively related to the exuberance and debilitation of kidney qi, but are also closely related to the exuberance and debilitation of qi and blood of the human body. Due to qi and blood insufficiencies in the body and deficiency of kidney essence, aged people often appear the condition of alopecia, and this is the objective law of birth, growth, robustness and age in the human body. The alopecia of youth not only affects the whole impression, but also may be a signal of kidney deficiency and blood deficiency occurring inside the body. According to traditional Chinese herb material science, the method for curing alopecia mostly adopts enriching yin and tonifying kidney.

There are many Chinese herbal materials used for enriching yin and tonifying the kidney. Among them, *Eclipta prostrata, Ligustrum Lucidum, Polygonum multiflorun*, etc. are most frequently applied for improving function of hair growth. Although there are old data records of these herbal material used for improving hair growth, there is no valid evidence for supporting the real effect so far.

According to the descriptions in ancient medical documents, *Eclipta prostrata* is the dried aerial part of Compositae plant, *Eclipta prostrata* L. It tastes both sweet and sour, and its medicinal property is classified as a little "cold." In addition, the effect of *Eclipta prostrata* enters the liver and kidney meridian, and function in cooling the blood to stop bleeding, nourishing liver and kidney, clearing heat and detoxifying. The main medical effect of the *Eclipta prostrata* is used for curing teeth loosing, premature whitening of hair, dizziness, tinnitus, waist and knee ache and weakness, yin deficiency and blood-heat, hematemesis, epistaxis, hematuria, blood dysentery, flooding and spotting blood, and traumatic injury bleeding. It is also said that *Eclipta prostrata* for internal use can blacken the beard and hair, and even promote the effect of hair growth occasionally. However, there is no evidence for supporting the mentioned medical effect.

*Ligustrum Lucidum* is the fruit of common holly which is classified as Oleaceae evergreen large bush, or dried mature fruit of small tree plant *Ligustrum Lucidum* A it. It tastes sweet yet also a little bitter, and its property is neutral and has no toxin. It goes back to liver and kidney meridian in body and tonifies kidney and nourishes yin, emolliates the liver, improves vision, strengthens heart, fortifies lumbar and knee, nourishes, relaxes the bowels, blackens the beard and hair, heavily settles, calms pain, reduces inflammation, releases heat, replenishes yin, tranquilizes, and clears weakness. It is often used for blackening the beard and hair in men, although its effects of hair growth are mentioned occasionally. However, there is no evidence for supporting the effect.

*Polygonum multiflorun* is dried root and stem of Polygonaceae Polygonum plant *Polygonum multiflorun* Thunb. It tastes sweet yet bitter and astringent, and its property is "warm." It goes back to meridian of liver, kidney, heart and lung etc, nourishes yin, energizes body, tonifies essence and blood, and tonifies the liver and kidney. It is also used in improving blood deficiency, sallowness, waist and knee ache and weakness, abnormal seminal emission, vaginal discharge, liver-kidney deficiency, head and eyes dizziness, premature whiteness of beard and hair, persistent malaria, ulcer, scrofula, intestinal dryness, constipation, insomnia, impotence, premature ejaculation, tinnitus, uterus bleeding etc. It is said that *Polygonum multiflorun* can blacken the beard and hair, although it is mentioned for its effects on hair growth occasionally. However, there is no evidence for supporting the effect.

SUMMARY OF THE INVENTION

The present invention provides a medical herb composition for reducing shedding of hair in a mammal, which comprises: a first herb material selected from the group consisting of Ginseng Radix, Astragali Radix, Batatatis Rhizoma, Zizyphi Fructus, *Tremella, Codonopsis Pilosula*, and the combination thereof; a second herb material selected from the group consisting of Angelicae Radix, Rehmanniae Preparata Radix, Longanae Arillus, Lycii Fructus, *Paeonia lactiflora*, and the combination thereof; and a third herb material selected from the group consisting of Rehmanniae Radix, *Ligustrum Lucidum, Eclipta prostrata, Dendrobium hancockii, Polygonum multiflorun* (i.e. *Dioscorea bulbifera* or *Cynanchum wilfordi*), and the combination thereof.

The ratio of the first, second, and third herb material of the medical herb composition of the present invention is not limited. Preferably, the percentage of the first herb material is 2~40 wt %; the percentage of the second herb material is 2~40 wt %; and the percentage of the third herb material is 20~96 wt %.

The first herb material of the medical herb composition of the present invention is preferably selected from the group consisting of Ginseng Radix, Astragali Radix, and the combination thereof. The second herb material of the medical herb composition of the present invention is preferably selected from the group consisting of Angelicae Radix, Rehmanniae Preparata Radix, and the combination thereof. The third herb material of the medical herb composition of the present invention is preferably selected from the group consisting of Rehmanniae Radix, *Eclipta prostrata, Ligustrum Lucidum, Polygonum multiflorun, Dioscorea bulbifera, Cynanchum wilfordi*, and the combination thereof.

The medical herb composition of the present invention can optionally be added with exterior-releasing herb material, diuretic herb material, heat-clearing herb material, and/or eliminating wetness-evil with herbs of fragrant flavour for increasing the function or effect.

The amount of exterior-releasing herb material of the medical herb composition of the present invention is not limited. Preferably, the adding amount of exterior-releasing herb material is 1~50 wt %. The more preferable adding amount for exterior-releasing herb material is 5~40 wt %. The amount of diuretic herb material of the medical herb composition of the present invention is not limited. Preferably, the adding amount of diuretic herb material is 1~50 wt %. The more preferable adding amount for diuretic herb material is 5~40 wt %. The amount of heat-clearing herb material of the medical herb composition of the present invention is not limited. Preferably, the adding amount of heat-clearing herb material is 1~70 wt %. The more preferable adding amount for heat-clearing herb material is 5~60 wt %. The amount of eliminating wetness-evil with herbs of fragrant flavour of the medical herb composition of the present invention is not limited. Preferably, the adding amount of eliminating wetness-evil with herbs of fragrant flavour is 1~40 wt %. The more preferable adding amount for eliminating wetness-evil with herbs of fragrant flavour is 2~30 wt %.

The exterior-releasing herb material applied in the medical herb composition of the present invention can be any conventional exterior-releasing herb material. Preferably, the exterior-releasing herb material is selected from the group consisting of Ledebouriellae Radix, Notopterygii Rhizoma, Cimicifugae Rhizoma, Allii Fistulosi Bulbus, Asari Herba Cum Radice, Ephedrae Herba, Perillae Folium, Zingiberis Rhizoma, and the combination thereof.

The diuretic herb material applied in the medical herb composition of the present invention can be any conventional diuretic herb material. Preferably, the diuretic herb material is selected from the group consisting of Alismatis Rhizoma, Polyporus, Atractylodis Rhizoma, Akebiae Caulis, Fangchi Radix, Boehmeriae Radix, and the combination thereof.

The heat-clearing herb material applied in the medical herb composition of the present invention can be any conventional heat-clearing herb material. Preferably, the heat-clearing herb material is selected from the group consisting of Puerariae Radix, Scutellariae Radix, Anemarrhenae Rhizoma, Glycyrrhizae Radix, Artemisiae Capillaris Herba, Rehmanniae Radix, Moutan Radicis Cortex, and the combination thereof.

The eliminating wetness-evil with herbs of fragrant flavour (or named dry dampness to fortify the spleen herb material, resolve dampness and enliven the spleen herb material) applied in the medical herb composition of the present invention can be any conventional eliminating wetness-evil with herbs of fragrant flavour. Preferably, the eliminating wetness-evil with herbs of fragrant flavour is selected from the group consisting of Atractylodis Rhizoma, Eupatorii Herba, Magnolia Cortex, Pogostemi Herb, and the combination thereof.

In the medical herb composition of the present invention, exterior-releasing herb material preferably is Ledebouriellae Radix extracts, Notopterygii Rhizoma extracts, Cimicifugae Rhizoma extracts, or the combination thereof; diuretic herb material preferably is Alismatis Rhizoma extracts, Polyporus extracts, Atractylodis Rhizoma extracts, or the combination thereof; heat-clearing herb material preferably is Puerariae Radix extracts, Scutellariae Radix extracts, Anemarrhenae Rhizoma extracts, *Glycyrrhizae Radix* extracts, Artemisiae Capillaris Herba extracts, or the combination thereof; eliminating wetness-evil with herbs of fragrant flavour preferably is Atractylodis Rhizoma extracts.

The medical herb composition of the present invention can further comprise an excipient, and also can be added with other pharmaceutical acceptable carriers. For example, the type of the medical herb composition for oral administration comprises capsule, tablet, emulsifier, liquid suspension, dispersing agent, and solvent. Taking the tablet as an example, the carrier for general use is lactose, cornstarch, lubricant, or magnesium stearate which is used as a basic additive. Oral administration capsule as drug administration type can made from lactose or cornstarch as an effective diluent. If it is necessary, the medicine can be added with appropriate sweetener, relish agent, or pigment. The medical herb composition of the present invention can further comprise an excipient, and suitable excipient for use can be any conventional one. Preferably, the excipient is cornstarch.

Besides, the present invention also provides a method for preparing a medical herb composition for reducing shedding of mammalian hair, which comprises following steps: (a) providing the first herb material selected from the group consisting of Ginseng Radix, Astragali Radix, Batatatis Rhizoma, Zizyphi Fructus, *Tremella, Codonopsis Pilosula*, and the combination thereof; the second herb material selected from the group consisting of Angelicae Radix, Rehmanniae Preparata Radix, Longanae Arillus, Lycii Fructus, *Paeonia lactiflora*, and the combination thereof; and the third herb material selected from the group consisting of Rehmanniae Radix, *Ligustrum Lucidum, Eclipta prostrata, Dendrobium hancockii, Polygonum multiflorun, Dioscorea bulbifera, Cynanchum wilfordi*, and the combination thereof; and (b) mixing the materials provided by step (a) to form a mixture. The mix ratio of the first, second, and third material is not limited. Preferably, the percentage of the first herb material is 2~40 wt %; the percentage of the second herb material is 2~40 wt %; and the percentage of the third herb material is 20~96 wt %.

The medical herb composition and the preparation of the same of the present invention can optionally further comprise a step of: providing exterior-releasing herb material, diuretic herb material, heat-clearing herb material, or/and eliminating wetness-evil with herbs of fragrant flavour in step (a). The amount of exterior-releasing herb material is not limited. Preferably, the amount of exterior-releasing herb material is 1~50 wt %. More preferably, the amount of exterior-releasing herb material is 5~40 wt %. The amount of diuretic herb material is not limited. Preferably, the amount of diuretic herb material is 1~50 wt %. More preferably, the amount of diuretic herb material is 5~40 wt %. The amount of heat-clearing herb material is not limited. Preferably, the amount of heat-clearing herb material is 1~70 wt %. More preferably, the amount of heat-clearing herb material is 5~60 wt %. The amount of eliminating wetness-evil with herbs of fragrant flavour is not limited. Preferably, the amount of eliminating wetness-evil with herbs of fragrant flavour is 1~40 wt %. More preferably, the amount of eliminating wetness-evil with herbs of fragrant flavour is 2~30 wt %.

The medical herb composition and the preparation of the same of the present invention can optionally further comprises a step of: providing an excipient, and mixing the excipient and the mixture, and the medicine can also be added with other pharmaceutical acceptable carriers when it is necessary.

The herb material mentioned by the medical herb composition and the preparation of the same of the present invention is Chinese herbal material (including the herb material of plant of different origin but having the same effect of medication recorded on the pharmacopoeia, or conventional alternative herb material), Chinese herbal material extracts, or the combination thereof. The extracts can be prepared according to conventional scientific Chinese herbal material preparation method, and the product can be water extracts, or alcohol extracts. Besides, extracts can be obtained by spray drying granulation or freeze drying granulation.

In the herbal material preparation method of the present invention, preferably, provided material is Chinese herbal material extracts, which are obtained by extraction separately; or provided material is Chinese herbal material, and after step (b) further comprises step (c) extracting the mixture to obtain the medical herb composition of the present invention. More preferably, after using water to carry out extraction and spray drying granulation to obtain each dried extracts, then each dried extract is mixed according to the ratio.

Taking the medical herb composition of the present invention acting as an oral administration drug, not only can reduce shedding of mammalian hair, but also can improve hair growth, and have the effect of improving microcirculation of skin to improve the mental condition of user, and obviously improve the skin condition and complexion of user.

BRIEF DESCRIPTION OF THE DRAWINGS

FIG. 1 is statistics of effects of *Eclipta prostrata* given to subjects after three months.
FIG. 2 is statistics of effects of prescription A1 given to subjects after three months.
FIG. 3 is statistics of effects of prescription A2 given to subjects after three months.
FIG. 4 is statistics of effects of prescription A3 given to subjects after three months.
FIG. 5 is statistics of effects of prescription A4 given to subjects after three months.
FIG. 6 is statistics of effects of prescription A5 given to subjects after three months.
FIG. 7 is statistics of effects of prescription A6 given to subjects after three months.

DETAILED DESCRIPTION OF THE PREFERRED EMBODIMENT

The preparation method of the present invention according to the preparation method of conventional scientifically concentrated traditional Chinese herb material, includes the steps of: extracting, isolating, condensing, drying etc. (as written in Sun Ten Journal of Medicine & Pharmacy) After obtaining scientifically concentrated traditional Chinese herb material powder from each herb extract, six prescriptions are prepared according to different materials and ratios (details as listed in Table 1). Then, the oral administration prescriptions are given to subjects who have conditions of hair shedding to carry out tests. Besides, the prescription of the present invention can also be mixed according to different material ratios, and then the herb materials are extracted, condensed, and dried to obtain the prescription at one time. Six prescriptions composed of each medical herb extract according to different materials and ratios are shown in Table 1.

TABLE 1

Prescriptions list used in the present invention

| Prescription | The first herb material (wt %) | The second herb material (wt %) | The third herb material (wt %) |
|---|---|---|---|
| A1 | Astragali Radix 30 wt % | Angelicae Radix 20 wt % | Rehmanniae Radix 50 wt % |
| A2 | Astragali Radix 40 wt % | Angelicae Radix 5 wt % | Eclipta prostrata 45 wt % |
| A3 | Astragali Radix 20 wt % | Angelicae Radix 35 wt % | Ligustrum Lucidum 45 wt % |
| A4 | Astragali Radix 10 wt % | Angelicae Radix 10 wt % | Rehmanniae Radix + Eclipta prostrata + Ligustrum Lucidum 80 wt % (1:1:1) |
| A5 | Ginseng Radix 15 wt % | Angelicae Radix 15 wt % | Ligustrum Lucidum 70 wt % |
| A6 | Astragali Radix 35 wt % | Rehmanniae Preparata Radix 35 wt % | Ligustrum Lucidum 30 wt % |

Besides, since it is said that *Eclipta prostrata, Ligustrum Lucidum, Polygonum multiflorun* etc. also have effects of reducing hair shedding, promoting hair growth, and blackening hair, the most frequently applied material, *Eclipta prostrata* is used as a contrast example (please see details in example 1).

The dosage of administration is calculated according to body weight. Each human body takes 0.5~1 g for every 10 Kg weight everyday (taking 1 g/10 Kg for first three months, follow-up taking 0.5 g/10 Kg). The curing effect is determined in three months as a period of treatment, according to individual perception and photo records as the determined standard of curing effect. For obtaining scientific data, the effects classified as 0~5 scores are shown. The classifying index for scoring includes following four items, i.e. evaluation of exempting alopecia, evaluation of growing hair (newgrown fuzz), evaluation of vitality, and evaluation of skin condition and complexion.

[Score Standard]
0 point: no improvement at all
1 point: rare improvement, barely detectable
2 point: slightly improved
3 point: definitely improved
4 point: obviously improved
5 point: very obviously improved or others can determine differences easily by naked eye

EXAMPLE 1

*Eclipta prostrata*

Six volunteers are tested in the present example. Subjects are given continuous oral administration of scientifically concentrated traditional Chinese herb material powder of *Eclipta prostrata*, and statistics are compiled three months later (see details in FIG. 1). The classifying index for scoring includes four items, i.e. evaluation of exempting alopecia, evaluation of growing hair (newgrown fuzz), evaluation of vitality, and evaluation of skin condition and complexion. The score of each item of the test in the present example is 1.0, 0.5, 0.7, and 0.7 point respectively, and the score indicates that the test result falls into the range of "rare improvement, that could be hard to detect". The medical effects of *Eclipta prostrata* for growing hair and exempting alopecia claimed by people are verified to be not clear in the present example. It is also shown that *Eclipta prostrata* has to cooperate with other medical herb materials to gain more valid curing effects.

EXAMPLE 2

Prescription A1

Nine volunteers are tested in the present example. Subjects are given continuous oral administration of scientifically concentrated traditional Chinese herb material powder of prescription A1 (Astragali Radix, Angelicae Radix, and Rehmanniae Radix, as listed in Table 1) and statistics are compiled three months later (see details in FIG. 2). The classifying index for scoring includes four items, i.e. evaluation of exempting alopecia, evaluation of growing hair (newgrown fuzz), evaluation of vitality, and evaluation of skin condition and complexion. The score of each item is 4.1, 2.4, 3.3, and 2.9 points respectively. Among them, the curing effect of exempting alopecia is very excellent, and the curing effect of growing hair (newgrown fuzz), vitality, and skin condition and complexion also meet to the requirement of definite improvement. The curing effect of the medical herb composition of the present invention tested and verified in the present example have curing effect far superior to that of single *Eclipta prostrata*.

The subject of the present example Mr. Chou, a 43-year-old male, began shedding hair on the calvaria with unknown reason 20 years ago. The boundary line of Mr. Chou's hair also moved back; the hair on the part of shedding grew thinner and thinner; and the hair started to shed when length reached about 1 to 2 cm. After taking prescription A1 for one month, Mr. Chou found that the amount of shedding hair had reduced, and his vitality had also improved. After taking prescription A1 for three months, Mr. Chou found that fuzz on calvaria thickened, and his family members also observed that his hair was clearly growing more. Moreover, the hair on his forehead also began to thicken. After taking the product for four months, the amount of shedding hair continuously reduced; the hair on calvaria and forehead turns thick; and the complexion became much ruddier than it was three months ago.

EXAMPLE 3

Prescription A2

Nine volunteers are tested in the present example. Subjects are given continuous oral administration of scientifically concentrated traditional Chinese herb material powder of prescription A2 (Astragali Radix, Angelicae Radix, and *Eclipta prostrata*, as listed in Table 1) and statistics are compiled three months later (see details in FIG. 3). The classifying index for scoring includes four items, i.e. evaluation of exempting alopecia, evaluation of growing hair (newgrown fuzz), evaluation of vitality, and evaluation of skin condition and complexion. The score of each item is 4.3, 2.9, 3.8, and 2.2 points respectively. Among them, the curing effect of exempting alopecia is very excellent, and the curing effect of growing hair (newgrown fuzz), vitality, and skin condition and complexion also meet the requirement of definite improvement. The curing effect of the medical herb composition of the present invention tested and verified in the present example have curing effect far superior to that of single *Eclipta prostrata*. In addition, the results in the present example shows that Rehmanniae Radix having similar effect as *Eclipta prostrata* (both classified as the third herb material) can be replaced with each other.

The subject of the present example Mr. Chiu, 31-year-old male, began to shed hair on both sides of forehead for unknown reason 1 year ago, but a dermatologist diagnosed that the symptom is Androgenetic alopecia (AGA) secondary. After Mr. Chiu had been taking prescription A2 for one month, his vitality improved, and the amount of shed hair reduced (the amount of shed hair reduced from 100 to 30-40 when shampooed). During taking herb material, Mr. Chiu had better vitality, and ruddy and good complexion. After he had been taking the herb material for three months, the hair on the shedding part of both sides of forehead is obviously denser than it was before.

EXAMPLE 4

Prescription A3

Nine volunteers are tested in the present example. Subjects are given continuous oral administration of scientifically concentrated traditional Chinese herb material powder of prescription A3 (Astragali Radix, Angelicae Radix, and *Ligustrum Lucidum*, as listed in Table 1) and statistics are compiled three months later (see details in FIG. 4). The classifying index for scoring includes four items, i.e. evaluation of exempting alopecia, evaluation of growing hair (newgrown fuzz), evaluation of vitality, and evaluation of skin condition and complexion. The score of each item is 4.3, 2.9, 4.1, and 3.4 points respectively. Among them, the curing effect of exempting alopecia and vitality are very excellent, and the curing effect of growing hair (newgrown fuzz), and skin condition and complexion also meet the requirement of definite improvement. The curing effects of the medical herb composition of the present invention tested and verified in the present example have curing effects far superior to that of single *Eclipta prostrata*. In addition, the results in the present example show that Rehmanniae Radix, *Eclipta prostrata*, and *Ligustrum Lucidum* (all classified as the third herb material) all have similar effect, and therefore can be replaced with each other.

The hair of Mr. Hsu, subject of the present example, 38-year-old male, began to become thinner and thinner 6 or 7 years ago, and the dermatologist diagnosed that the symptom is Androgenetic alopecia (AGA) tertiary. After Mr. Hsu had been taking prescription A3 for one month, his vitality improved. Moreover, Mr. Hsu feels that his body is full of energy, and the amount of shed hair has greatly reduced. After taking the herb material for two months, he found that the hair had obviously grown denser than it did on the forehead before.

EXAMPLE 5

Prescription A4

Ten volunteers are tested in the present example. Subjects are given continuous oral administration of scientifically concentrated traditional Chinese herb material powder of prescription A4 (Astragali Radix, Angelicae Radix, *Ligustrum Lucidum*, Rehmanniae Radix, and *Eclipta prostrata* as listed in Table 1) and statistics are compiled three months later (see details in FIG. 5). The classifying index for scoring includes four items, i.e. evaluation of exempting alopecia, evaluation of growing hair (newgrown fuzz), evaluation of vitality, and evaluation of skin condition and complexion. The score of each item is 4.4, 3.2, 4.0, and 2.9 points respectively. Among them, the curing effects of exempting alopecia and vitality are very excellent, and the curing effect of growing hair (newgrown fuzz), and skin condition and complexion also meet the requirement of definite improvement. In the third herb material of the medical herb composition of the present invention, *Ligustrum Lucidum*, Rehmanniae Radix, and *Eclipta prostrata* are used at the same time in the present example, since the three herb materials are inexpensive, and have advantages on the manufacturing procedure. Therefore, the present prescription is a good example.

The subject of the present example Mr. Yen, 60-year-old male, has shed hair for many years. It appears that there is no hair on the entire calvaria, but a lot of fuzz still can be seen by use of an examining instrument for hair follicles of scalp. Mere fuzz cannot grow long enough and fall out, causing baldness, a classic symptom of AGA.

After Mr. Yen had been taking prescription A4 for one and half months, his vitality improved, and his complexion turned ruddy and good. When the result was tracked by photographing, it is found that fuzz which can be seen by naked eye has grown on the bald part of calvaria.

After taking the herb material for three months, it is found that fuzz on the calvaria had obviously thickened. This shows that the period of hair growth has been lengthened, and the hair cannot be shed prematurely.

After taking the herb material for five months, Mr. Yen expressed that his gray hair amount had reduced. By examining hair follicles of scalp, it is found that the roots of gray hairs has turned black unexpectedly. It shows that the medical herb composition of the present invention has obvious mending effects for hair follicles, so gray hair can turn black.

EXAMPLE 6

Prescription 5

Seven volunteers are tested in the present example. Subjects are given continuous oral administration of scientifically concentrated traditional Chinese herb material powder of prescription A5 (Ginseng Radix, Angelicae Radix, and *Ligustrum Lucidum* as listed in Table 1) and statistics are compiled three months later (see details in FIG. 6). The classifying index for scoring includes four items, i.e. evaluation of exempting alopecia, evaluation of growing hair (newgrown fuzz), evaluation of vitality, and evaluation of skin condition and complexion. The score of each item is 4.3, 3.0, 3.3, and 2.5 points respectively. Among them, the curing effect of exempting alopecia is very excellent, and the curing effect of growing hair (newgrown fuzz), vitality, and skin condition and complexion also meet the requirement of definite improvement. The curing effect of the medical herb composition of the present invention tested and verified in the present example has curing effect far superior to that of single *Eclipta prostrata*. In addition, the results in the present example show that Ginseng Radix having similar effect as Astragali Radix (both classified as the first herb material) have can be replaced with each other.

The subject of the present example Ms. Yeh, 26-year-old female, began to shed hair in a large amount for unknown reasons three and half months ago before taking the herb material. Before Ms. Yeh started to take herb material, almost all her hair had been shed. Only several black hair remained, and hair on her arms had almost completely been shed. According to Ms. Yeh's description: her hair started to shed from April, 2006. At first, the hair shed as a small circle shape on her head, but then the shedding speed accelerated. By the end of June, almost all her hair had been shed. She went to see a doctor, and the doctor gave injection into part of her scalp, but it was inefficient. This is generally called "having one's head shaved by ghost" condition. Even though, many examinations were performed by doctors, the cause of disease could not be determined, and the symptom could not be cured.

After Ms. Yeh had been taking prescription A5 of the present invention for one month, white and gold fuzz obviously grew all over the head, and black fuzz also grew on the parts of arms and eyebrows, and former black long hair continuously shed.

After she had been taking prescription A5 for two months, black fuzz grew on the area both left and right sides above her ears. Moreover, former eyebrows and hair continuously shed. But there was a lot of light color fuzz growing, the fuzz closest to the area above left and right ears had lengthened, and some hair follicles' front end of former gold fuzz had black hair traits. All light color fuzz lengthened, and fuzz on the part of eyebrows started to grow.

After she had been taking prescription A5 for three months, thin black hair in the neighborhood above left and right ears obviously grew, and former black hair all shed. In addition, the whole vitality obviously improved, and the blood circulation was better than it was before.

After she had been taking prescription A5 for four months, the area of black hair above left and right ears had broadened. Black hair growing on calvaria continuously thickened and lengthened. The phenomenon is especially obvious on the part of hindbrain, and black fuzz also grew on other parts.

After she had been taking prescription A5 for five months, black short hair grew on most of her scalp, and the hair continuously lengthened. There was obvious black hair on calvaria, hindbrain, and behind the ears.

After she had been taking prescription A5 for six months, there was mostly all black hair on the part which hair had grown and the hair turned thick and long. Black fuzz grew on the part of eyebrows.

After she had been taking prescription A5 for seven months, the hair grew almost all over her head, and fuzz also grew on the arms.

After she had been taking prescription A5 for eight months, the hair continuously lengthened; general shedding reduced; blood circulation improved; and complexion was much ruddier.

EXAMPLE 7

Prescription A6

Six volunteers are tested in the present example. Subjects are given continuous oral administration of scientifically concentrated traditional Chinese herb material powder of prescription A6 (Astragali Radix, Rehmanniae Preparata Radix, and *Ligustrum Lucidum*, as listed in Table 1) and statistics are compiled three months later (see details in FIG. 7). The classifying index for scoring includes four items, i.e. evaluation of exempting alopecia, evaluation of growing hair (newgrown fuzz), evaluation of vitality, and evaluation of skin condition and complexion. The score of each item is 3.8, 2.5, 3.8, and 2.8 points respectively. Among them, the curing effect of exempting alopecia is very excellent, and the curing effect of growing hair (newgrown fuzz), vitality, and skin condition and complexion also meet the requirement of definite improvement. The curing effect of the medical herb composition of the present invention tested and verified in the present example has curing effect far superior to that of single *Eclipta prostrata*. In addition, the results in the present example show that Angelicae Radix having similar effect as Rehmanniae Preparata Radix (both classified as the second herb material) can be replaced with each other.

Through the test results illustrated above, it is inferred that: the medical herb composition of the present invention not only reduces hair shedding, but also improves vitality and skin condition and complexion efficiently. The effects are quite excellent, and much superior to single nourishing herb material, such as *Eclipta prostrata, Polygonum multiflorun*, and *Ligustrum Lucidum* which are generally used for blackening and growing hair.

Besides, according to the test results illustrated above, the medical herb composition can be added with exterior-releasing herb material (preferably, exterior-releasing herb material is Ledebouriellae Radix, Notopterygii Rhizoma, Cimicifugae Rhizoma, or the combination thereof), diuretic herb material (preferably, diuretic herb material is Alismatis Rhizoma, Polyporus, Atractylodis Rhizoma, or the combination thereof), heat-clearing herb material (preferably, heat-clearing herb material is Puerariae Radix, Scutellariae Radix, Anemarrhenae Rhizoma, Glycyrrhizae Radix, Artemisiae Capillaris Herba, or the combination thereof), or/and eliminating wetness-evil with herbs of fragrant flavour (preferably, eliminating wetness-evil with herbs of fragrant flavour is Atractylodis Rhizoma) depends on condition to develop fitting effects.

The examples illustrated above are only cited for explaining for convenience. The scope of the claim advocated by the present invention should be taken by claims as the standard, but is not only limited to examples illustrated above. Although the present invention has been explained in relation to its preferred embodiment, it is to be understood that many other possible modifications and variations can be made without departing from the scope of the invention as hereinafter claimed.

What is claimed is:

1. A medical herb composition for reducing shedding of hair of a mammal, consisting essentially of:
   a first herb material which is Astragali Radix;
   a second herb material which is Angelicae Radix, and
   a third herb material which is a combination of Rehmanniae Radix, *Ligustrum Lucidum*, and *Eclipta prostrata*,
   wherein the percentage of the first herb material is 2~40 wt %; the percentage of the second herb material is 2~40 wt %; and the percentage of the third herb material is 20~96 wt %.

2. The medical herb composition of claim 1, wherein the herb materials are extracts obtained by spray drying or freeze drying granulation.

3. The medical herb composition of claim 1, wherein the herb materials are water extracts or alcohol extracts.

4. The medical herb composition of claim 1, wherein the composition is formulated with an excipient.

5. The medical herb composition of claim 1, wherein the medical herb composition for reducing shedding of mammalian hair has effects of promoting hair growth.

6. The medical herb composition of claim 1, wherein the medical herb composition for reducing shedding of mammalian hair has effects of improving skin condition.

7. The medical herb composition of claim 1, wherein the medical herb composition for reducing shedding of mammalian hair is an oral administration preparation.

8. A method for preparing a medical herb composition for reducing shedding of mammalian hair, consisting essentially of:
   (a) providing a first herb material which is Astragali Radix; providing a second herb material which is Angelicae Radix, and a third herb material which is a combination of Rehmanniae Radix, *Ligustrum Lucidum*, and *Eclipta prostrata*; and
   (b) mixing the herb material from step (a) to a mixture, wherein the percentage of the first herb material is 2~40 wt %; the percentage of the second herb material is 2~40 wt %; and the percentage of the third herb material is 20~96 wt %.

9. The method for preparing a medical herb composition of claim 8, wherein the composition is formulated with an excipient.

10. The method for preparing a medical herb composition of claim 8, wherein the herb materials are extracts obtained by spray drying or freeze drying granulation.

11. The method for preparing a medical herb composition of claim 8, wherein the herb materials are water extracts or alcohol extracts.

12. The method for preparing a medical herb composition of claim 8, wherein the medical herb composition for reducing shedding of mammal hair is an oral administration preparation.

13. A method for preparing a medical herb composition for reducing shedding of mammalian hair, consisting essentially of:
   (a) providing a first herb material which is Astragali Radix; providing a second herb material which is Angelicae Radix, and a third herb material which is a combination of Rehmanniae Radix, *Ligustrum Lucidum*, and *Eclipta prostrata*;
   (b) mixing the herb material from step (a) to a mixture, wherein the percentage of the first herb material is 2~40 wt %; the percentage of the second herb material is 2~40 wt %; and the percentage of the third herb material is 20~96 wt %; and
   (c) extracting the mixture;

14. The method for preparing a medical herb composition of claim 13, wherein the medical herb composition for reducing shedding of mammal hair is an oral administration preparation.

* * * * *